United States Patent
Park et al.

(10) Patent No.: US 7,319,323 B2
(45) Date of Patent: Jan. 15, 2008

(54) DEVICE AND METHOD USING MAGNETIC PATTERN ON DISK

(75) Inventors: Chang-Min Park, Portland, OR (US); Shriram Ramanathan, Cambridge, MA (US); Kenneth Cadien, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 83 days.

(21) Appl. No.: 11/394,160

(22) Filed: Mar. 31, 2006

(65) Prior Publication Data

US 2007/0229078 A1    Oct. 4, 2007

(51) Int. Cl.
*G01V 3/00* (2006.01)
(52) U.S. Cl. .................. 324/300; 324/307; 324/314
(58) Field of Classification Search ............. 324/300, 324/307, 314, 318, 322
See application file for complete search history.

(56) References Cited

U.S. PATENT DOCUMENTS

| | | | |
|---|---|---|---|
| 2003/0090664 A1* | 5/2003 | Amonette et al. | 356/432 |
| 2004/0150396 A1* | 8/2004 | Simmonds et al. | 324/239 |

* cited by examiner

*Primary Examiner*—Louis M. Arana
(74) *Attorney, Agent, or Firm*—Darby & Darby P.C.

(57) ABSTRACT

An embodiment of the invention relates to a device for performing NMR or ESR analysis. The device comprises a detection unit, a magnet, and a disk having a magnetic pattern. The detection unit comprises a sample holding space for holding a sample and a microcoil for detecting NMR or ESR signals generated within the sample. The magnet generates a static magnetic field within the sample. The disk and magnetic pattern, when rotating, generate an excitation magnetic field, which, together with the static magnetic field, creates an NMR or ESR within the sample. Other embodiments of the invention encompass methods for performing NMR or ESR analysis using the device and methods of making such devices.

62 Claims, 4 Drawing Sheets

DEVICE AND METHOD USING MAGNETIC PATTERN ON DISK

RELATED APPLICATIONS

This application is related to application Ser. No. 11/319,755, entitled "Integrated on-chip NMR and ESR device and method for making and using the same;" and to application Ser. No. 11/319,773, entitled "Portable NMR device and method for making and using the same," both filed Dec. 29, 2005, and both of which are incorporated herein by reference.

FIELD OF INVENTION

The embodiments of the invention relate to NMR or ESR devices, methods of making such devices, and methods of performing NMR or ESR analysis using such devices. More specifically, the embodiments relate to devices and methods that combine on-chip NMR or ESR technology and magnetic patterns on a rotatable disk that perform versatile and/or convenient NMR or ESR analysis with design flexibility. The invention transcends several scientific disciplines such as nuclear chemistry and physics, engineering, microelectronics, analytical chemistry, and medical diagnostics.

BACKGROUND

Nuclear Magnetic Resonance (NMR) and, to a lesser degree, Electron Spin Resonance (ESR) are widely used in chemical analysis and medical diagnostics. NMR is a physical phenomenon that occurs when the nuclei of certain atoms that are subject to a static magnetic field are exposed to a second oscillating magnetic field. The oscillating magnetic field, often generated by an electromagnet, is also called a perturbing or excitation magnetic field. Some nuclei experience this phenomenon, and others do not, dependent upon whether they possess a property called spin. ESR, which is also called Electron Paramagnetic Resonance (EPR), is a physical phenomenon analogous to NMR, but instead of the spins of the atom's nuclei, electron spins are excited in an ESR. Because of the difference in mass between nuclei and electrons, weaker static magnetic fields and higher frequencies for the oscillating magnetic fields are used, compared to NMR.

The current devices using the NMR or ESR principle have at least two drawbacks. First, the sizes of the devices are too big. For example, typical NMR spectrometers are bench-top models. Thus, the current spectrometers are too big to be used in field applications or at home environment. Second, the current NMR devices require a large amount of sample, which not only is infeasible for certain applications, but also hinders activities such as mixing and heating of the sample required for many analysis. Thus, there is a need for a miniaturized, integrated, and versatile NMR or ESR device that can perform on-site, flexible, rapid, sensitive, and/or efficient analysis.

DETAILED DESCRIPTION

Figure 1:
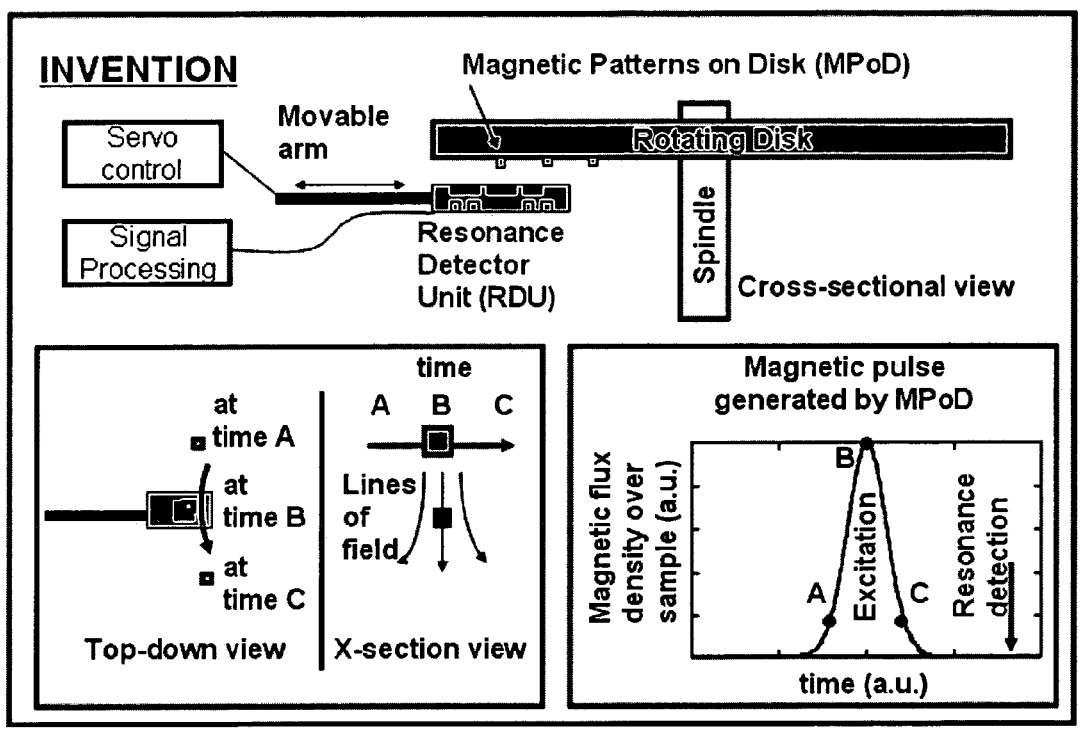
FIG. 1 illustrates an embodiment of the invention that comprises a disk with magnetic patterns, a resonance detector unit, a servo-control mechanism, and a signal processing unit.

The embodiments of the invention relate to a device comprising an on-chip NMR or ESR detection unit, a magnet, and a rotatable disk with a magnetic pattern for performing chemical analysis and medical diagnostics. Specifically, the detection unit comprises a sample holding space and an associated microcoil; the magnet is to generate a static magnetic field across the sample holding space; and the magnetic pattern on the rotating disk is to generate an excitation magnetic field across the sample holding space such that an NMR or ESR is generated within a sample contained in the space. The signals from the NMR or SER are detected by the microcoil. The device may further comprise servo-mechanical components and mechanisms to control the locations and movements of the detection unit, the magnet, and the disk.

The embodiments of the invention also relate to a method of performing NMR or ESR analysis using the device and to a method of making the device. The detection unit of the embodiments of the invention may be part of an integrated device that also serves as a microarray or macroarray, an integrated circuit, a microfluidic device, a MEMS, or a combination. Therefore, samples contained or processed by the device may be also analyzed by the integrated NMR or ESR device and the signals processed for analysis. If necessary, the signals from the NMR may be transmitted to another device for further analysis, such as NMR or ESR spectroscopy and Magnetic Resonance Imaging (MRI).

As used in the specification and claims, the singular forms "a", "an" and "the" include plural references unless the context clearly dictates otherwise. For example, the term "an array" may include a plurality of arrays unless the context clearly dictates otherwise.

A "disk" or "disc" refers to an object that has a flattened cylinder shape. Although a disk used herein is usually rigid, it may also be flexible, such as being bendable. The disk could be made from many suitable materials, including but not limited to metals, polymers, silicon, and glass. The size and thickness of the disk will depend upon the specific device and its applications desired. Specific types of disks commercially available and readily adaptable include optical discs, compact discs (CDs), digital versatile discs (DVDs), laserdisc, magneto-optical discs, minidisk, digital multilayer disks, fluorescent multilayer disc, universal media discs, floppy disks, and hard drive disks. The disks should be adaptable to mechanical and/or electrical controls such that they are able to rotate at controlled and desired speeds and be placed at desired locations. Further, magnetic materials should be able to be attached to the disks to form desired patterns.

A "magnetic pattern" on a disk refers to one or more of magnetic materials or "magnetic members" attached on a surface of the disk according to a pre-designed fashion. The magnetic members are usually discretely located on the surface, although they may also be interconnected in certain situations. A magnetic member is usually small in size and can be defined by the area that it occupies on the surface and the thickness, or the biggest perpendicular distance from any point on the member to the surface of the disk. A magnetic member is further defined by its distance to the center of the disk. Thus, when the disk is rotating, a certain magnetic member will rotate at a specific linear speed, based on the rotating speed of the disk and the member's distance from the center of the disk. The rotation will also create a unique circular "track" for a specific magnetic member. As discussed herein, a rotating magnetic member is capable of generating an excitation magnetic field within a sample in a sample holding space that is on or near the track of the magnetic member.

"Disk rotation," "rotation" or "rotating" refers to turning of a disk around its center, or imaginative center, in a substantially smooth fashion and without noticeable wobbling. In other words, when rotating, a disk should remain substantially within a plane. The speed of a disk rotation can be measured by revolution per minute or "rpm." The movement of an object, such as a magnetic member, on the disk can be measured by the linear travel speed, which can be determined by the disk's rotation speed and the distance of the object to the center of the disk. As discussed herein, a rotating magnetic member can generate magnetic pulses, and the ability of the magnetic member to generate an excitation magnetic field depends, in part, on its linear travel speed.

A "substrate" refers to a material or a combination of materials upon and/or within which other or additional materials are formed, attached, or otherwise associated with according to a predetermined fashion. A substrate often provides physical and functional support to the other or additional materials such that, together, they form part or whole of a functional device. A substrate may be a combination of two or more other substrates, which, due to the combination, have become an identifiable new substrate. In the embodiments of the invention, the substrate may comprise metal, silicon, glass, or polymeric materials. In more specific embodiments, the substrate comprises an integrated material, such as a microfluidic device or an integrated circuit die.

A "microcoil" is a coil, or one or more connected loops, having at least one dimension in the micrometer ($\mu$m), or less than $10^{-3}$ meter (mm), scale. A microcoil usually comprises a thin material wound or gathered around a center or an imaginative center into spiral, helical or other shapes. A microcoil is defined by the material itself, the shape of the windings, and the separation between each windings. Solenoid type microcoils are multiple spiral wire loops, which may or may not be wrapped around a metallic core. A Solenoid type microcoil produces a magnetic field when an electrical current is passed through it and can create controlled magnetic fields. A Solenoid type microcoil can produce a uniform magnetic field in a predetermined volume of space. A "planar" microcoil is a microcoil with its windings substantially remained in an actual or imaginative plane.

A "microchannel" is a channel, groove, or conduit having at least one dimension in the micrometer ($\mu$m), or less than $10^{-3}$ meter (mm), scale. Although microchannels are typically straight along their length, they may contain angles and curves of different degrees along their length. Although the microchannels typically have rectangular cross-sections, they may also have other shapes of cross-sections, such as circle. The microchannels are usually suitable for fluidic communications, such as carrying through a biological liquid. The microchannels are often part of an integrated device, such a microfluidic device or an integrated circuit such that liquid flowing through the microchannels are in a controlled pattern and able to be analyzed as desired.

As used in the embodiments of the invention, "associated with" or "in association with" means that two or more objects are so situated that the desired results or effects are achieved. For example, a microcoil is "associated" with a space for holding a liquid sample when the microcoil is so situated that it will achieve the desired effect of generating an excitation magnetic field and/or detecting an NMR or ESR signal within at least a portion of a sample in the space. Similarly a magnet is also "associated" with the space and the microcoil if it is capable of generating a static magnetic field across at least a portion of the space. A number of factors will be considered when associating the microcoil or the magnet with the space, including whether the magnet is on the detection unit substrate, the sizes and shapes of the substrate, the type and size of the microcoil and the magnet, the size and location of the associated space, the desired strengths of the excitation magnetic field and the static magnetic field and, and the volume within which the desired NMR or ESR will be effectuated. As disclosed herein, the specific locations of the magnet and microcoil on the detection unit, or substrate, will be determined based on the specific analysis desired by a person skilled in the art.

As used herein, "dimension" or "dimensions" are the parameters or measurements required to define the shape and/or size, such as height, width, and length, of an object. As used herein, the dimension of a two-dimensional object, such as a rectangle, a polygon, or a circle, is the longest straight-line distance between any two points on the object. Therefore the dimension of a circle is its diameter; a rectangle its diagonal, and a polygon its longest diagonal. The dimension of a three-dimensional object is the longest straight-line distance between any two points on the object. The dimensions used herein are usually measured by centimeters (cm), millimeters (mm), and micrometers ($\mu$m), and nanometers (nm).

A "microfluidic device" is a device that has one or more microchannels. A microfluidic device may be part of an integrated device, such as an integrated separation or detection equipment or an integrated circuit. Fluids used in microfluidic devices include whole blood samples, bacterial cell suspensions, protein or antibody solutions and various buffers and saline. Microfluidic devices can be used to obtain many interesting measurements, including fluid mechanical properties, cellular and molecular diffusion coefficients, fluid viscosity, pH values, chemical and biological binding coefficients and enzyme reaction kinetics. Other applications for microfluidic devices include cell and molecule detection and separation, capillary electrophoresis, isoelectric focusing, immunoassays, flow cytometry, sample injection of proteins for analysis via mass spectrometry, DNA analysis, cell manipulation, and cell separation. In the embodiment of the invention, magnetic materials and technologies are incorporated into the microfluidic devices for applications such as cell and biomolecule detection and separation.

The use of microfluidic devices to conduct biomedical assays has many significant advantages. First, because the volume of fluids within these channels is very small, usually several nano-liters, the amount of reagents and analytes required for the assays is quite small. This is especially significant for expensive reagents. The fabrications techniques used to construct microfluidic devices, discussed in more details herein, are relatively inexpensive and are very amenable both to highly elaborated, multiplexed devices and also to mass production, such as in an integrated circuit die. In manners similar to that for microelectronics, microfluidic technologies also enable the fabrication of highly integrated devices for performing different functions on the same substrate chip. Embodiments of the invention helps create integrated, portable clinical diagnostic devices for home and bedside use, thereby eliminating time consuming laboratory analysis procedures.

In the embodiments of the invention, the flow of a fluid through a microfluidic channel, or microchannel, can be characterized by the Reynolds number (Re), defined as $$Re = LV_{avg}\rho/\mu$$

where L is the most relevant length scale, $\mu$ is the fluid viscosity, $\rho$ is the fluid density, and $V_{avg}$ is the average velocity of the flow. For many microchannels, including channels with a rectangular cross-section, L is equal to 4A/P where A is the cross-sectional area of the channel and P is the wetted perimeter of the channel. Due to the small dimensions of microchannels, the Re is usually much less than 100, often less than 1.0. In this Reynolds number regime, flow is completely laminar and no turbulence occurs. The transition to turbulent flow generally occurs in the range of Reynolds number 2000. Laminar flow provides a means by which molecules can be transported in a relatively predictable manner through microchannels.

As used herein, "magnetic," "magnetic effect," and "magnetism" refer to the phenomena by which one material exert an attractive or repulsive force on another material. Although theoretically all materials are influenced to one degree or another by magnetic effect, those skilled in the art understand that magnetic effect or magnetism is only recognized for its detectability under the specific circumstance.

As used herein, a "permanent magnet" is a material that has a magnetic field without relying upon outside influences. Due to their unpaired electron spins, some metals are magnetic when found in their natural states, as ores. These include iron ore (magnetite or lodestone), cobalt, and nickel. A "paramagnetic material" refers to a material that attracts and repels like normal magnets when subject to a magnetic field. Paramagnetic materials include aluminum, barium, platinum, and magnesium. A "ferromagnetic material" is a material that can exhibit a spontaneous magnetization. Ferromagnetism is one of the strongest forms of magnetism and is the basis for all permanent magnets. Ferromagnetic materials include iron, nickel, and cobalt. A "superparamagnetic material" is a magnetic material that exhibits a behavior similar to that of a paramagnetic material at temperatures below the Curie or the Neel temperature.

An "electromagnet" is a type of magnet in which the magnetic field is produced by a flow of electric current. The magnetic field disappears when the current ceases. A simple type of electromagnet is a coiled piece of wire that is electrically connected. An advantage of an electromagnet is that the magnetic field can be rapidly manipulated over a wide range by controlling the electric current. In the embodiments of the invention, ferromagnetic or non-magnetic materials are used to form the electromagnets.

An "array," "macroarray" or "microarray" is an intentionally created collection of substances, such as molecules, openings, microcoils, detectors and/or sensors, attached to or fabricated on a substrate or solid surface, such as glass, plastic, silicon chip or other material forming an array. The arrays can be used to measure the expression levels of large numbers, e.g., tens, thousands or millions, of reactions or combinations simultaneously. An array may also contain a small number of substances, e.g., a few or a dozen. The substances in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

An array of microcoils is a collection of microcoils fabricated on a substrate, such as silicon, glass, or polymeric substrate. Each of the microcoils may be associated or corresponded with a sample space across which the microcoil is capable of generating an oscillating magnetic field as part of an NMR analysis. The sample space may be a space for holding a liquid sample or a spot for immobilizing certain molecules, such as DNAs and proteins. The microcoil arrays may be a microarray or a macroarray depending on the sizes or the microcoils and the associated sample spaces.

A DNA microarray is a collection of microscopic DNA spots attached to a solid surface forming an array. DNA microarrays can be used to measure the expression levels of large numbers of genes simultaneously. In a DNA microarray, the affixed DNA segments are known as probes, thousands of which can be used in a single DNA microarray. Measuring gene expression using microarrays is relevant to many areas of biology and medicine, such as studying treatments, disease and developmental stages.

"Solid support" and "support" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "molecule" generally refers to a macromolecule or polymer as described herein. However, microchannels or arrays comprising single molecules, as opposed to macromolecules or polymers, are also within the scope of the embodiments of the invention.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

The term "biomolecule" refers to any organic molecule that is part of or from a living organism. Biomolecules include a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles.

As used herein, "biological cells" and "cells" are interchangeable, unless otherwise clearly indicated, and refer to the structural and functional units of all living organisms, sometimes called the "building blocks of life." Cells, as used herein include bacteria, fungi, and animal mammalian cells. Specifically included are animal blood cells, such as red blood cells, white blood cells, and platelets.

The term "target," "target molecule," or "target cell" refers to a molecule or biological cell of interest that is to be analyzed or detected, e.g., a nucleotide, an oligonucleotide, a polynucleotide, a peptide, a protein, or a blood cell. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires and nanoparticles. The target molecule or cell may be magnetically tagged, or labeled to facilitate their detection and separation.

The term "probe" or "probe molecule" refers to a molecule that binds to a target molecule or cell for the analysis of the target. The probe or probe molecule is generally, but not necessarily, has a known molecular structure or sequence. The probe or probe molecule is generally, but not necessarily, attached to a solid support of the microfluidic device or array. The probe or probe molecule is typically a nucleotide, an oligonucleotide, a polynucleotide, a peptide, or a protein, including, for example, cDNA or pre-synthesized polynucleotide deposited on the array. Probes molecules are biomolecules capable of undergoing binding or molecular recognition events with target molecules or cells. A probe or probe molecule can be a capture molecule.

The term "capture molecule" refers to a molecule that is immobilized on a surface. The capture molecule is generally, but not necessarily, binds to a target or target molecule or cell. The capture molecule is typically a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be magnetically or fluorescently labeled DNA or RNA. In specific embodiments of the invention, the capture molecule may be immobilized on the surface of a magnetic tunnel junction sensor, which itself is part of an integrated device, such as a microfluidic device or an integrated circuit. The capture molecule may or may not be capable of binding to just the target molecule or cell, or just the probe molecule.

The terms "die," "polymer array chip," "DNA array," "array chip," "DNA array chip," or "bio-chip" are used interchangeably and refer to a collection of a large number of probes arranged on a shared substrate which could be a portion of a silicon wafer, a nylon strip or a glass slide.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

When the biomolecule or macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is a molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex.

The term "chip" or "microchip" refers to a small device or substrate that comprises components for performing certain functions. A chip includes substrates made from silicon, glass, metal, polymer, or combinations and capable of functioning as a microarray, a macroarray, a microfluidic device, a MEMS, and/or an integrated circuit. A chip may be a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components. In the embodiments of the invention, as discussed herein, microchannels, microfluidic devices, and magnetic tunnel junction sensors can also be integrated into a microchip.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow Microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost. In the embodiments of the invention, as discussed herein, MEMS devices are further integrated with microchannels, microfluidic devices, and/or magnetic tunnel junction sensors, such that, together, they perform separation and detection function for biological cells and biomolecules.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "nanomaterial" as used herein refers to a structure, a device or a system having a dimension at the atomic, molecular or macromolecular levels, in the length scale of approximately 1-1000 nanometer (nm) range. Preferably, a nanomaterial has properties and functions because of the size and can be manipulated and controlled on the atomic level.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

One embodiment of the invention relates to a device for performing NMR or ESR analysis. The device comprises a detection unit, a magnet, and a disk comprising a magnetic pattern. In the embodiment, the detection unit comprises a microcoil and a space for holding a sample; the magnet is to generate a static magnetic field across at least a portion of the space; and the magnetic pattern on the disk is to generate an excitation magnetic field across at least a portion of the space. According to the embodiment, the static magnetic field and the excitation magnetic field are capable of creating Nuclear Magnetic Resonance (NMR) or Electron Spin Resonance (ESR) within a sample contained in the space; and wherein the microcoil is capable of detecting signals from the NMR or ESR.

In one embodiment, the detection unit integrates a sample holding space and a microcoil for detecting NMR or ESR signals occur within a sample in the space. The sample holding space and the microcoil may be supported by or integrated into a substrate. The magnet for generating the necessary static magnetic field can be placed either on the substrate or at a location near the substrate. The magnetic pattern on the disk, when rotating at a pre-designed speed, generates a excitation magnetic field with a sample in the space.

In a specific embodiment of the invention, the detection unit or the substrate comprises silicon, glass, a polymeric material, metal, or a combination thereof. More specifically, the detection unit may either comprise or be connected to an integrated circuit, a MEMS device, a microarray, a macroarray, a multi-well plate, a microfluidic device, or a combination thereof. In other words, the embodiment can be integrated into or connected to a wide range of materials used in a variety of existing devices.

Silicon is a suitable material for forming micro-channels coupled with microelectronics or other microelectromechanical systems (MEMS). It also has good stiffness, allowing the formation of fairly rigid microstructures, which can be useful for dimensional stability. In a specific embodiment of the invention, the detection unit or substrate comprises an integrated circuit (IC), a packaged integrated circuit, and/or an integrated circuit die. For example, the substrate may be a packaged integrated circuit that comprises a microprocessor, a network processor, or other processing device. The substrate may be constructed using, for example, a Controlled Collapse Chip Connection (or "C4") assembly technique, wherein a plurality of leads, or bond pads are internally electrically connected by an array of connection elements (e.g., solder bumps, columns).

Specific materials useful as the substrate also include, but not limited to, polystyrene, polydimethylsiloxane (PDMS), glass, chemically functionalized glass, polymer-coated glass, nitrocellulose coated glass, uncoated glass, quartz, natural hydrogel, synthetic hydrogel, plastics, metals, and ceramics. The substrate may comprise any platform or device currently used for carrying out immunoassays, DNA or protein microarray analysis. Thus, the substrate may comprise a microarray or a macroarray, a multi-well plate, a microfluidic device, or a combination thereof.

In another embodiment, the detection unit comprises circuitry that is capable of amplifying or processing the NMR or ESR signals detected by the microcoil. Any suitable conventional circuits may be used and integrated into the substrate for amplifying and/or processing, including filtering, the NMR or ESR signals detected and collected by the microcoil. The integrated circuitry may be able to generate NMR or ESR spectra independently or connected to an external device for generating the device.

In another embodiment of the invention, the sample is a liquid, a gel, a solid, a gas, or a mixture thereof. Therefore, the embodiment of the invention can accommodate samples in different physical states. In a specific embodiment, the sample is a liquid or in a liquid or solution state. In another embodiment, the space for holding a sample comprises a reservoir, a microchannel, an opening, a surface, or a combination thereof. The embodiment accommodates a variety of applications in which an NMR or ESR is involved. For example, the sample holding space may be a reservoir, an opening void, or a surface that can hold a liquid sample. In such cases, the sample holding space may be an open reservoir or surface, or a substantially closed void with an opening for sample input. The design of the space depends not only on the specific analysis to be done, but also on how to best situate and design the sample holding space in relation to the associated magnet and microcoil, as discussed herein.

According another embodiment, the space for holding a sample, such as a liquid sample, may also be the whole or part of a microchannel fabricated on the detection unit, or substrate. Depending on the specific requirement, the microchannel may be open (a trench) or closed. The microchannel typically comprises an inlet and an outlet, but may also comprise other opening for fluidic communication. In another embodiment, the microchannel comprise two or more inlets and at least one outlet such that different reactants may be introduced into the channel from different inlets and mixed at a mixing section within the channel for specific chemical reaction. Furthermore, the microchannel may comprise more than two inlets and more than one mixing sections such that more than one reaction may occur within different sections of the mircochannel according predetermined manners. As discussed herein, the microchannel is designed in consideration with its relations with the associated magnet and microcoil and with the location of the disk and magnetic patterns to achieve the desired NMR or ESR.

In the embodiments of the invention, device and the detection unit can accommodate a wide range of sample volume, including very small amount of samples. In one embodiment, the space for holding a liquid sample has a volume of from about 1.0 nL to about 1.0 mL. In another embodiment, the space has a volume of from about 10 nL to about 10 µL. As understood by a person skilled in the art, actual sample volumes will depend on the nature of the analysis to be conducted, in addition to the limitation of the device. Also, the volume of the sample that actually experiences the NMR or ESR phenomenon will depend on the design and dimension of the device as well as the analysis being conducted. In cases where the space for holding the liquid sample is a microchannel having two inlets and one outlet, the total sample holding space may be substantially larger than the volume that is under NMR or ESR effect. For example, the total channel volume, excluding the inlets and outlet, may be about 1.0 µm while the volume under the microcoil, or the NMR or ESR effect, may be about only 10 nL to 100 nL.

In one embodiment of the invention, the magnet, whether on or near the substrate, comprises a permanent magnet or an electromagnet. As disclosed herein, the permanent magnet or electromagnet generates a static magnetic field across at least a portion of the space for holding a liquid sample. Materials suitable for use as the permanent magnet or electromagnet include permanent magnetic materials, ferromagnetic materials, paramagnetic materials, and non-magnetic metals. When a ferromagnetic material is used for the magnet, an external magnetic field is used to magnetize the material. Further, when either a ferromagnetic or non-magnetic material is used for the magnet, an electrical current is applied to the material to create an electromagnet. In one embodiment of the invention, the magnet comprises one or more of iron, nickel, cobalt, a rare-earth material such as neodymium, copper, aluminum, and mixtures thereof. More specifically, a Neodymium-Iron-Boron type magnet can be used.

In the embodiment, the static magnetic field, together with the excitation magnetic field generated by the rotating disk and magnetic pattern, is capable of creating NMR or ESR within a liquid sample contained in the space. In this regard, the magnet is "associated" with the space for holding a liquid sample, meaning that the magnet is so situated that it will achieve the desired effect. A number of factors will be considered when associating the magnet with the space, including whether the magnet is on the substrate, the sizes and shapes of the detection unit, the size of the magnet, the sizes and locations of the associated space and microcoil, the size, location and rotation speed of the disk and the magnetic pattern, the desired strength of the static magnetic field, and the volume within which the desired NMR or ESR will be effectuated. In a specific embodiment, the magnet is placed near or adjacent to the space for holding a liquid sample. The specific type, size, strength, and location of the magnet on the substrate will be determined based on the specific analysis desired by a person skilled in the art.

Embodiments of the present invention can be adapted to perform either NMR or ESR analysis. As disclosed herein, ESR occurs according to similar principles as NMR, except that unpaired electron spins are detected in ESR, whereas unpaired nuclear spins are detected in NMR. Therefore, ESR and NMR spectra reveal different aspects of the target's structure. Unpaired electrons are rare in natural states as most stable molecules, such as those in nature biological samples, have a closed-shell configuration without a suitable unpaired spin, ESR has not been as widely used as NMR in analytical chemistry and medical diagnostics. In addition, ESR sometimes requires spin labeling or artificial introduction of unpaired electron spins. However, ESR is useful in detecting species that have unpaired electrons, such as free radical, if the species is an organic molecule, or contain transition metal ions if the species is an inorganic complex.

As disclosed herein, ESR has higher sensitivities as compared to NMR and it requires a lower strength for the static magnetic field. A static magnetic field strength of less than 0.5 Tesla (T) is usually required for ESR, whereas a strength of larger than 0.5 T, or more typically larger than 1.0 T, is required for NMR. On the other hand, ESR has a higher resonance frequency, usually larger than 1.0 GHz, as compared to less than 500 MHz for NMR. Also, for NMR, pulse wave measurement and technique are commonly used and that traditional continuous NMR is rare. For ESR, both continuous and pulse wave measurement and technique are used. Although the embodiments of the invention focus on pulse wave measurement, the embodiments also encompass continuous wave techniques. As disclosed herein, the differences between ESR and NMR means that materials selections are different for an ESR or NMR device, and that different electronic circuitries are required to detect, collect, and/or process the signals from the ESR or NMR.

In a specific embodiment, the magnet is capable of generating a static magnetic field strength of from about 0.01 Tesla (T) to about 30 T, or more specifically, from about 0.05 T to about 10 T. As disclosed herein, for NMR, a static magnetic field strength of 0.1 T or more may be required. Usually, a static magnetic field strength of 0.5 T or more is used in an NMR. Thus, in a specific embodiment, the magnet is capable of generating a static magnetic field strength of from about 0.1 T to about 5.0 T. In another specific embodiment, the magnet is capable of generating a static magnetic field strength of from about 0.1 T to about 2.0 T. Also as disclosed herein, for ESR, a static magnetic field strength of 1.0 T or less may be required. Usually, a static magnetic field strength of 0.5 T or less is used in an ESR. Thus, in a specific embodiment, the magnet is capable of generating a static magnetic field strength of from about 0.1 T to about 0.5 T. In another specific embodiment, the magnet is capable of generating a static magnetic field strength of from about 0.3 T to about 0.5 T.

In the embodiments of the invention, many conductive materials are suitable for the microcoil. In the embodiments, the microcoil can be used for either detecting the NMR or ESR signals or generating an excitation magnetic field across at least a portion of the sample holding space. The selection of materials for the microcoil depends on several factors including the type and size of the coil, the desired strength of NMR or ESR signals to be detected, the size and location of space for holding a liquid sample, the shape, size and nature of the substrate, the nature and location of the magnet, and the location and rotating speed of the disk and magnetic pattern. The conductivity of the material is important to the selection. In one embodiment of the invention, the microcoil comprises copper, aluminum, gold, silver, or a mixture thereof.

In the embodiments of the invention, the microcoil is "associated" with the space for holding a sample, meaning that meaning that the microcoil is so situated that it will achieve the desired effect of detecting NMR or ESR within at least a portion of the space. A number of factors will be considered when associating the microcoil with the space, including the type and size of the microcoil, the sizes and locations of the associated space and magnet, the desired strength of the static magnetic field and the excitation magnetic field, and the volume within which the desired NMR or ESR will be effectuated. In a specific embodiment, the microcoil is placed near or adjacent to the space for holding a liquid sample. The specific type, size, strength, and location of the microcoil on the substrate will be determined based on the specific analysis desired by a person skilled in the art.

In one embodiment of the invention, the microcoil is a Solenoid type coil. Solenoid type microcoils are multiple spiral wire loops, which may or may not be wrapped around a metallic core. A Solenoid type microcoil, in addition to serving as a detection circuit, produces a magnetic field when an electrical current is passed through it and can create controlled magnetic fields. In the embodiment of the invention, the Solenoid type microcoil can produce a uniform magnetic field in a predetermined volume of the space.

In another embodiment of the invention, the microcoil is a planar spiral coil, which is a microcoil with its windings substantially remained in an actual or imaginative plane. In the embodiment, the microcoil is wound around a center, which often is also the center; or on the same axis of the center, of the associated space for holding a liquid sample and expands in a spiral like manner. The winding may take many different forms, depending on the needs of the specific device and analysis. For example, the winding may take a generally circular, square, or rectangular shape.

In the embodiments of the invention, a planar microcoil is defined, in part, by its inner-area dimension, the number of windings, and the winding separation. The inner-area of a microcoil refers to the area at the center of the microcoil where there is no winding and around which the microcoil is wound. The shape of the inner-area is usually not perfectly regular, although it is often similar to a circular, rectangular, or square shape. The dimension of the inner-area is described herein by the length of the parameter of the area. The number of windings as used herein refers to the number of times the microcoil is wound around the inner-area. As used herein, the winding separation refers to the distance between two adjacent windings.

In one embodiment of the invention, the planar spiral microcoil comprises an inner-area dimension of from about 10 µm to 10 mm, about 1 to 100 windings, and a winding separation of about 1 µm to 500 µm. In another embodiment, the microcoil comprises an inner-area dimension of from about 100 µm to 1.0 mm, about 1 to 30 windings, and a winding separation of about 10 µm to 100 µm. In another specific embodiment, the microcoil has a cross-section dimension of from about 0.01 µm to about 100 µm.

In the embodiments of the invention, a disk having a magnetic pattern is used to generate an excitation magnetic field across at least a portion of a sample in the sample holding space. According to the embodiment, the disk can be rotated at a variety of different speeds. As the disk rotates, the magnetic pattern on the disk is able to generate magnetic pulses within certain areas. Therefore, when placed near the sample holding space, a rotating disk can generate an desired excitation magnetic field across at least a portion of the space if the size and rotating speed of the disk and the nature and location of the magnetic pattern are controlled in a desired manner. Thus, according to the embodiments, it is no longer necessary to use microcoils and the associated circuitry to generate excitation magnetic field to create an NMR or ESR.

According to an embodiment of the invention, the disk could be made from many suitable materials, including but not limited to metals, polymers, silicon, and glass. The size and thickness of the disk will depend upon the specific device and its applications desired. Specific types of disks commercially available and readily adaptable include optical discs, compact discs (CDs), digital versatile discs (DVDs), laserdisc, magneto-optical discs, minidisk, digital multilayer disks, fluorescent multilayer disc, universal media discs, floppy disks, and hard drive disks. The disks should be adaptable to mechanical and/or electrical controls such that they are able to rotate at controlled and desired speeds and be placed at desired locations. Further, magnetic materials should be able to be attached to the disks to form desired patterns.

In a specific embodiment, the disk comprises metal, polymer, silicon, glass, or a combination thereof. More specifically, the disk may comprise aluminum, gold, copper, silver, cobalt, platinum, chromium, iron, a metal oxide, a polycarbonate, or a combination thereof. According to another embodiment, the disk is capable of storing data related to the NMR or ESR signal.

In another embodiment, the disk has a diameter ranging from about 1.0 cm to about 20 cm. More specifically, the disk has a diameter ranging from about 2.0 cm to about 10 cm. The thickness of the disk may range from about 0.1 mm to about 10 mm. In one embodiment, the thickness of the disk ranges from about 1.0 mm to about 3.0 mm.

According to the embodiments of the invention, a magnetic pattern on a disk encompasses one or more of magnetic materials, or magnetic members, attached on a surface of the disk according to a pre-designed fashion. The magnetic members are usually discretely located on the surface, although they may also be interconnected in certain situations. A magnetic member is usually small in size and can be defined by the area that it occupies on the surface and its thickness, or the biggest perpendicular distance from any point on the member to the surface of the disk. A magnetic member is further defined by its distance to the center of the disk. Thus, when the disk is rotating, a certain magnetic member will rotate at a specific linear speed, based on the rotating speed of the disk and the member's distance from the center of the disk. The rotation will also create a unique circular "track" for a specific magnetic member. As discussed herein, a rotating magnetic member is capable of generating an excitation magnetic field within a sample in a sample holding space that is on or near the track of the magnetic member.

In one embodiment of the invention, the magnetic pattern comprises one or more magnetic members attached to a surface of the disk. According to the embodiment, each of the magnetic members occupies an area on the surface of the disk and has a thickness measured by the biggest perpendicular distance from a point on the magnetic member to the surface of the disk. The nature, numbers, and locations of the magnetic members define the magnetic pattern on the disk. For example, a specific magnetic pattern may comprise one, two, three, or more magnetic members located at predetermined locations on the disk to achieve the goal of generating desired excitation magnetic fields across different sample holding spaces or different locations in a single sample holding space.

In one embodiment, the magnetic members comprise iron, nickel, cobalt, copper, aluminum, platinum, palladium, or a combination thereof. In another embodiment, the magnetic members comprise a cobalt alloy, a cobalt and platinum alloy, or a cobalt and palladium alloy.

In another embodiment, the area occupied by a magnetic member on a disk has a circular, rectangular, or cubical shape. In a specific embodiment, the area has a dimension ranging from about 1.0 nm to about 1000 mm. More specifically, the area has a dimension ranging from about 10 nm to about 5000 µm, or from about 0.1 µm to about 1000 µm.

In one embodiment, the thickness of a magnetic member ranges from 1.0 nm to about 500 mm. In another embodiment, the thickness ranges from about 10 nm to about 50 mm, or from 0.1 µcm to about 1000 µm.

In the embodiments of the invention, a magnetic member is further defined by its location on the disk, specifically, its distance from the center, or the imaginative center, of the disk. In one embodiment, there is only one magnetic member located at a given distance from the center of the disk. In another embodiment, there are two or more magnetic members located at a given distance from the center of the disk. In still another embodiment, two or more magnetic members are located at different distances from the center of the disk and form a straight line with the center of the disk.

In an embodiment of the invention, the distances from the magnetic members to the center of the disk range from about 1.0 cm to about 20 cm. In another embodiment, the distances from the magnetic members to the center of the disk range from about 2.0 cm to about 10 cm.

According to another embodiment of the invention, existing technologies can be used to construct the devices of the invention. For example, silicon process technologies can be used to construct or fabricate the detection unit of the embodiments of the invention, such that the sample holding space, microcoil can be constructed on a substrate that may also comprise an integrated circuit and/or microfluidic mechanisms. In another embodiment, servo-mechanical components and mechanisms can be used to control the location and movement of the disk and the detection unit such that the desired static and excitation magnetic fields and the associated NMR or ESR effects are generated.

FIGS. 1-4 illustrate various embodiments of the invention. In FIG. 1, a device comprising a detection unit, or resonance detector unit, and a rotating disk with magnetic patterns is shown. As illustrated, the detection unit comprises a sample holding space, a permanent magnet, and a microcoil. The rotating disk with magnetic patterns is situated near and over the detection unit and is placed on a spindle, such as a disk-drive spindle, at its center. The detection unit comprises a pair of permanent magnets located nest to the sample holding space, as shown and explained in more detail in FIGS. 2 and 3. The detection unit is further connected with a servo-control unit, which controls the location and movement of the detection unit, and a signal processing unit, which collects, analysis, and/or process signals detected by the detection unit.

As shown in FIG. 1, when the disk rotates or spins around the spindle, one or more of the magnetic members of the magnetic patterns on the disk will appear directly over the sample holding space. As shown in more detail in the lower left box of FIG. 1, the specific magnetic member appears near and directly over the sample holding space at times A, B and C and generates a magnetic field. Thus, the rotation of the disk over the detection unit and the sample holding space and the periodic appearance of the specific magnetic member over the space, at a desired frequency, generate a magnetic pulse or excitation in the space, as illustrated in the lower right box of FIG. 1. As a result, a sample contained in the sample holding space, already under a strong static magnetic field created by the permanent magnets, experiences NMR or ESR effects, which can be detected and captured by the microcoil in the detection unit and further analyzed and/or processed.

Figure 2:
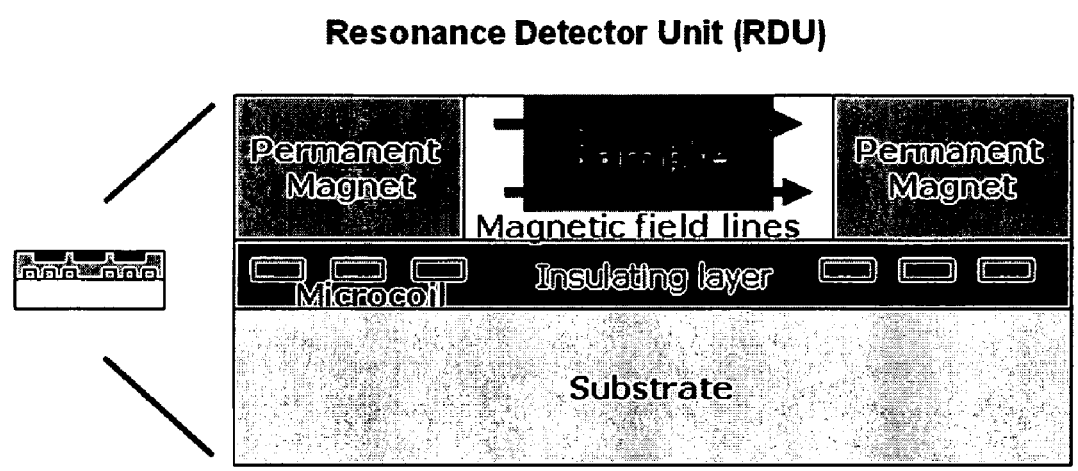
FIG. 2 illustrates a more detailed cross-section view of the resonance detector unit that comprises a substrate, a sample holding space, permanent magnets, and microcoils.
Figure 3:
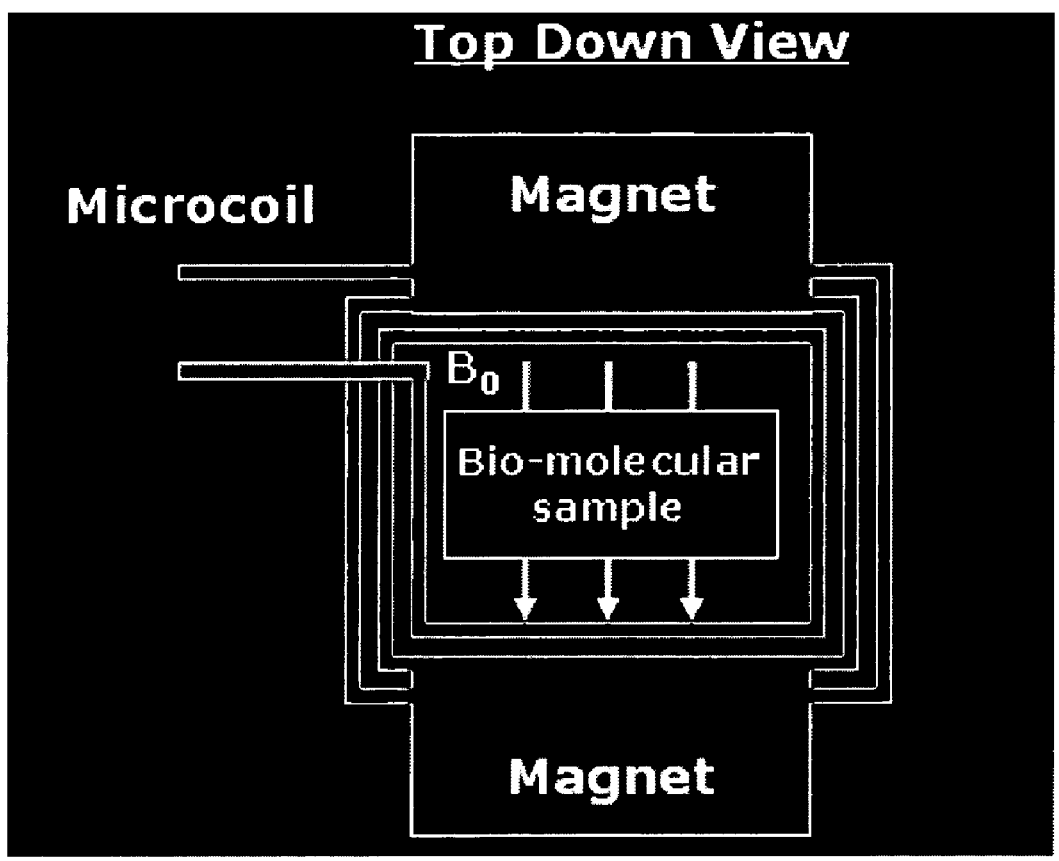
FIG. 3 illustrates a more detailed top-down view of the resonance detector unit.

FIGS. 2 and 3 illustrate a more detailed cross-section view and top-down view of an embodiment of the detection unit, or the resonance detector unit. As shown, the unit includes a space for holding a sample, such as a liquid sample, an associated microcoil, and a pair of built-in permanent magnets that generate a static magnetic field, $B_0$, across the sample holding space, which may contain a bio-molecular sample. As shown in FIGS. 2 and 3, the magnets are attached to a substrate through an insulating layer and are located next to the sample holding space. A planar microcoil is located just beneath the sample holding space and wound around the space, the center of which serves as an imaginative center of the windings. The windings of the microcoil are imbedded in the insulating layer, which is attached to the substrate. As shown in the figures, the microcoil is wound in a square shaped and spiral like manner around the center. As disclosed herein, the microcoil may also be wound around the center in circular shaped manners.

Figure 4:
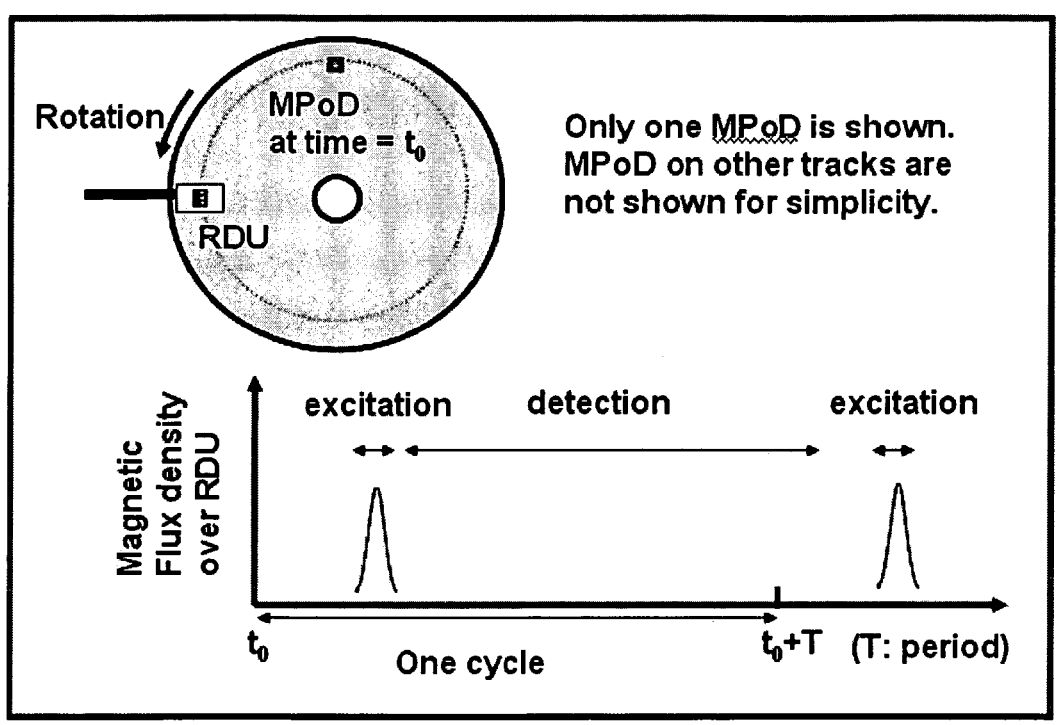
FIG. 4 illustrates a more detailed view of the disk with magnetic patterns.

FIG. 4 further illustrates an embodiment of the invention. A device comprising a detection unit, or resonance detector unit (RUD), and a disk with magnetic patterns is shown. For simplicity, only one magnetic member of the magnetic pattern on disk is shown. As illustrated, when the disk rotates, the magnetic member rotates on a track that intersects with the sample holding space on the detection unit. The lower graph illustrates the magnetic flux density over the detection unit (RDU), especially the sample holding space of the RDU, as a function of time.

As shown in FIG. 4, assuming a starting time at $t_0$, when the magnetic member is approximately a quarter of a rotation from the RDU, and a single rotation, or period, time of T, the magnetic excitation and detection are shown in the graph. The frequency of the excitation, when the magnetic member is directly over the sample holding space, depends on linear travel speed of the magnetic member. As discussed herein, the linear travel speed of a specific magnetic member on a disk depends on the rotation speed of the disk, e.g., as measured by rpm, and the distance from the member to the center of the disk. Thus, for a given disk, a specific magnetic pattern can be designed so that, according to the rotating speed of the disk and the distances of the magnetic members to the center of the disk, the magnetic members of the magnetic pattern on disk can produce distinct excitation magnetic fields across distinct sample holding spaces or distinct regions in a sample holding space.

Another embodiment of the invention relates to a device comprising a detection unit that comprises an array of sample holding spaces for holding liquid samples. In a specific embodiment, each of the spaces has a volume of from about 10 nL to about 100 µL. In one embodiment, the magnetic pattern on disk is capable of generating an excitation magnetic field across at least a portion of the space; and a magnet capable of generating a static magnetic field across at least two of the spaces. According to another embodiment, the magnet is capable of generating a static magnetic field across the at least two spaces.

According to one embodiment, in which the detection unit comprises an array of sample holding spaces, the static magnetic field and the excitation magnetic field are capable of creating NMR or ESR within a sample contained in each of the at least two of the spaces. In another embodiment, each of the at least two of the spaces is associated with a microcoil capable of detecting signals from the NMR or ESR. The sample may be a liquid, gel, solid, gas, or mixture. Variations of the embodiment encompass a detection unit, or substrate, that also comprises microarray or macroarray of microcoils and the associated sample holding space or spaces on the substrate. The microcoils and the spaces may be formed on or near the surface of the substrate using methods disclosed herein.

According to one embodiment, the detection unit further comprises a magnet capable of generating a static magnetic field across at least two of the spaces for holding a sample. In the embodiment, the magnet is integrated into the substrate of the detection unit and is so designed and situated that it can generate the required static magnetic field across a portion or the whole of the sample holding spaces. Alternatively, according to another embodiment, the magnet is located near the detection unit. In the embodiments, suitable conventional NMR or ESR magnets may be used according to the design of the device and the specific analysis to be carried out.

Suitable magnets include permanent magnets or electromagnets. As disclosed herein, the permanent magnet or electromagnet generates a static magnetic field across at least a portion of the spaces for holding a liquid sample. Materials suitable for use as the permanent magnet or electromagnet include permanent magnetic materials, ferromagnetic materials, paramagnetic materials, and non-magnetic metals. When a ferromagnetic material is used for the magnet, an external magnetic field is used to magnetize the material. Further, when either a ferromagnetic or non-magnetic material is used for the magnet, an electrical current is applied to the material to create an electromagnet. In one embodiment of the invention, the magnet comprises one or more of iron, nickel, cobalt, a rare-earth material such as neodymium, copper, aluminum, and mixtures thereof. More specifically, a Neodymium-Iron-Boron type magnet can be used.

In the embodiment, the static magnetic field, together with the excitation magnetic field generated by the magnetic pattern on disk, is capable of creating NMR or ESR within a liquid sample contained in each of at least two of the spaces. In this regard, the magnet is "associated" with the spaces, meaning that the magnet is so situated that it will achieve the desired effect in the at least two spaces. A number of factors will be considered when associating the magnet with the space, including the size of the magnet, the sizes and locations of the associated spaces, microcoils, the magnetic pattern on disk, the desired strength of the static magnetic field, and the volume within which the desired NMR or ESR will be effectuated. In a specific embodiment, the magnet is placed near or adjacent to the spaces for holding liquid samples. The specific type, size, strength, and location of the magnet on the substrate will be determined based on the specific analysis desired by a person skilled in the art.

In one embodiment, the detection unit comprises silicon, glass, a polymeric material, metal, or a combination thereof. In another embodiment, the detection unit comprises an integrated circuit, a MEMS device, a microarray, a macroarray, a multi-well plate, a microfluidic device, or a combination thereof. Further, the dete3ction unit may comprise circuitry that is capable of amplifying or processing the NMR or ESR signals detected by the microcoils.

In a specific embodiment of the invention, the detection unit, or substrate, comprises an array of spaces for holding samples and wherein each of at least a portion of the microcoils is capable of generating an excitation magnetic field across one of the spaces. According to the embodiment, the substrate comprises an array of sample holding spaces and their associated microcoils. The design of the sample holding space/microcoil array is made according to the specific analysis to be carried out. For example, specific samples can be put into the sample holding spaces, and analysis can be carried out with the help of the magnetic pattern on disk and the associated microcoils, as disclosed herein.

In another embodiment of the invention, the magnetic pattern on disk is capable of generating an excitation magnetic field across a plurality of the spaces, or distinct portions of one or more of the spaces. According to the embodiment, the spaces for holding a liquid sample are associated with the magnetic pattern on disk and with an array of microcoils. The magnetic patter is designed such that a magnetic member is associated with a distinct sample holding space or a distinct portion of, or a spot on, a sample holding space. The design of the microcoil array and the space is made according to the specific analysis. For example, probe or capture molecules can be attached to or associated with the individual microcoils to carry out specific DNA or protein analysis, as disclosed herein.

According to another embodiment of the invention, each of at least a plurality of the spaces for holding samples comprises a reservoir, a microchannel, an opening, a surface, or a combination thereof. The embodiment accommodates a variety of applications in which an NMR or ESR is involved. For example, the sample holding space may be a reservoir, an opening void, or a surface that can hold a liquid sample. In such cases, the sample holding space may be an open reservoir or surface, or a substantially closed void with an opening for sample input. The design of the space depends not only on the specific analysis to be done, but also on how to best situate and design the sample holding space in relation to the associated magnet and microcoil, as discussed herein.

According to the embodiment, the space for holding a liquid sample may also be the whole or part of a microchannel fabricated on the substrate. Depending on the specific requirement, the microchannel may be open (a trench) or closed. The microchannel typically comprises an inlet and an outlet, but may also comprise other opening for fluidic communication. In another embodiment, the microchannel comprise two or more inlets and at least one outlet such that different reactants may be introduced into the channel from different inlets and mixed at a mixing section within the channel for specific chemical reaction. Furthermore, the microchannel may comprise more than two inlets and more than one mixing sections such that more than one reactions may occur within different sections of the mircochannel according predetermined manners. As discussed herein, the microchannel is designed in consideration with its relations with the associated magnet and microcoil to achieve the desired NMR or ESR.

In the embodiments of the invention, the integrated on-chip NMR or ESR detection unit or substrate can accommodate a wide range of sample volume, including very small amount of samples. In one embodiment, the space for holding a liquid sample has a volume of from about 1.0 nL to about 10 mL, or more specifically, from about 0.1 µL to about 5.0 mL. In the embodiment, the sample holding space may be associated with a specifically designed magnetic pattern on disk, each magnetic member of which is capable of generating an excitation magnetic field across a distinct portion or spot on the space. In another embodiment, the substrate comprises an array of sample holding spaces and each of the spaces has a volume of from about 10 nL to about 10 µL. As understood by a person skilled in the art, actual sample volumes will depend on the nature of the analysis to be conducted, in addition to the limitation of the device. Also, the volume of the sample that actually experiences the NMR or ESR phenomenon will depend on the design and dimension of the device as well as the analysis being conducted.

Another embodiment of the invention relates to a method of performing an NMR or ESR analysis. The method comprises: (1) providing a device that comprises a detection unit, a magnet, and a disk, wherein the detection unit comprises a microcoil and a space for holding a sample and the disk comprises a magnetic pattern; (2) providing a sample within the space; (3) using the magnet to generate a static magnetic field across at least a portion of the sample; (4) rotating the disk to generate an excitation magnetic field across at least a portion of the sample; and (5) detecting signals from the sample by using the microcoil.

In one embodiment, the static magnetic field and the excitation magnetic field create Nuclear Magnetic Resonance (NMR) or Electron Spin Resonance (ESR) within the sample, which may be in a liquid, gel, solid, gas, or a mixture state. In another embodiment, the method further comprises amplifying, processing, or analyzing the signals detected by the microcoil. The detection unit may comprise a circuitry capable of detecting, processing, or analyzing the signals from the sample. According to another embodiment, the method comprises generating an NMR or ESR spectroscopy of the liquid sample, or storing data related to the NMR or ESR signals in the disk. Also, the providing of the liquid sample within the space comprises introducing two or more different samples into the space.

In one embodiment of the NMR or ESR analysis method, the providing of the device comprises using a servomechanism to control the location and movement of the detection unit, the magnet, and/or the disk. In the embodiment, conventional servomechanisms can be used such that the arrangement of the detection unit, including the sample holding space and microcoil, the magnet, and the disk with magnetic pattern is suited to create the desired NMR or ESR for a sample in the sample holding space.

According to one embodiment, the rotating of the disk is at a speed of from about 10 rpm to about 2000 rpm. More specifically, the rotating of the disk is at a speed of from about 100 rpm to about 1000 rpm, or from about 200 rpm to about 600 rpm.

In the embodiment, samples suitable for the NMR or ESR analysis may contain any types of substances that can be analyzed through an NMR or ESR analysis. The substances include organic or inorganic molecules, macromolecule, biological cells, biomolecules such as proteins, peptides, nucleotides, polynucleotides, DNAs, RNAs, and substances containing free radicals radical or transition metal ions. Further, the volume of the sample may range from 1.0 nL to about 1.0 mL or, more specifically, from 10 nL to about 10 µL.

In one embodiment of the NMR or ESR analysis method, the detection unit comprises an array of spaces for holding samples and the magnetic pattern on disk comprises a plurality of magnetic members. According to the embodiment, each of at least a portion of the magnetic members is used to generate an excitation magnetic field across at least a plurality of the sample holding spaces or a plurality of distinct portions of a sample holding space. In another embodiment, the detection unit comprises an array of microcoils associated with the array of sample holding spaces and each of at least a portion of the microcoils is used to detect NMR or ESR signals from a sample in one of the spaces.

According to one embodiment, the detection unit or substrate further comprises a magnet capable of generating a static magnetic field across at least a plurality of the sample holding spaces. In the embodiment, the magnet is integrated into the substrate and is so designed and situated that it can generate the required static magnetic field across a portion or the whole of the plurality of sample holding spaces. Alternatively, according to another embodiment, the magnet is placed near the detection unit. In the embodiments, suitable conventional NMR or ESR magnets may be used according to the design of the device and the specific analysis to be carried out. Further, suitable magnets include permanent magnets or electromagnets.

According to one embodiment, each of at least a portion of the microcoils or sample holding spaces on the detection unit is associated with a biomolecule. In a specific embodiment, the biomolecule a DNA and is capable of hybridizing with a complementary DNA. NMR signals from the DNA hybridization is detected by at least a portion of the microcoils.

The above embodiments of the invention may also be regarded as integrating the plurality of microcoils and, in certain cases, the spaces for holding samples into a macroarray or microarray, such as a DNA array. In the embodiments, as discussed herein, multiple microcoils and the associated spaces are formed on or near the surface of the substrate and form an array to perform certain analysis. When incorporated into a DNA array, the microcoils or sample holding spaces are further associated with or attached to the probe molecule or DNA probe, such that, when the DNA target and the probe hybridize, the whole or part of the hybridized molecule can be detected through NMR microcoils.

As disclosed herein, compound and molecules suitable for the NMR or ESR analysis by the embodiments of the invention include proteins, peptides, and, specifically, nucleic acids (DNA and RNA), which can form double-stranded molecules by hybridization, that is, complementary base pairing. For example, in an embodiment of the invention, a molecular probe, such as a DNA probe, is associated with or attached to a sample reservoir or microcoil, which is located near or on the surface of, or otherwise integrated into, the substrate. The specificity of nucleic acid hybridization is such that the detection of molecular and/or nanomaterials binding events can be done through measurements of the NMR signals by the microcoils and other integrated or external components. This specificity of complementary base pairing also allows thousands of hybridization to be carried out simultaneously in the same experiment on a DNA chip (also called a DNA array).

Molecular probes are immobilized on the surface of individual or individually addressable reservoirs and/or microcoils through surface functionalization techniques. The microcoils allow the NMR or ESR signals to be detected and/or measured. The probe in a DNA chip is usually hybridized with a complex RNA or cDNA target generated by making DNA copies of a complex mixture of RNA molecules derived from a particular cell type (source). The composition of such a target reflects the level of individual RNA molecules in the source. The NMR or ESR signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example herein below. However, other equivalent conventional procedures can, of course, also be used.

Another embodiment of the invention relates to a method of making an NMR or ESR device. The method comprises: (1) fabricating a space for holding a sample on a substrate; (2) fabricating a microcoil on the substrate, the microcoil being associated with the space; (3) attaching a magnet to the substrate, the magnet being capable of generating a static magnetic field across at least a portion of the space; and (4) fabricating a magnetic pattern on a disk, the magnetic pattern being capable of generating an excitation magnetic field across at least a portion of the space. According to the embodiment, the static magnetic field and the excitation magnetic field are capable of creating Nuclear Magnetic Resonance (NMR) or Electron Spin Resonance (ESR) within a sample contained in the space and the microcoil is capable of detecting signals from the NMR or ESR.

In one embodiment of the invention, fabricating of the sample holding space or fabricating of the microcoil comprises combining two or more solid support to form the substrate. According to the embodiment, the sample is a liquid, a gel, a solid, a gas, or a mixture thereof. In another embodiment, the method for fabricating a device further comprises forming circuitry on the substrate such that the circuitry is capable of amplifying or processing the NMR or ESR signals detected by the microcoil. Also, the method may further comprise providing servo-mechanical components to control the locations and movements of the substrate, the magnet, and the disk.

The NMR or ERS devices of the embodiments of the invention may be formed by any suitable means of manufacture, including semiconductor manufacturing methods, microforming processes, molding methods, material deposition methods, etc., or any suitable combination of such methods. In certain embodiments one or more of the magnets, microcoils, and circuitries on the detection unit, or substrate, may be formed via semiconductor manufacturing methods on a semiconductor substrate. Thin film coatings may be selectively deposited on portions of the substrate surface. Examples of suitable deposition techniques include vacuum sputtering, electron beam deposition, solution deposition, and chemical vapor deposition. The coatings may perform a variety of functions. For example, the coatings may be used to increase the hydrophilicity of a surface or to improve high temperature properties. Conductive coatings may be used to form the microcoils. Coatings may be used to provide a physical barrier on the surface, e.g. to retain fluid at specific sites on the surface.

In one embodiment of the invention, the substrate is made through combining two or more smaller substrates or solid support. Specifically, the fabricating of the sample holding space, the attaching of the magnet, or the fabricating of the microcoil may involve combining two or more smaller substrates to form the substrate or detection unit.

The substrate used in the embodiments of the invention may comprise various materials including, but not limited to silicon, glass, metal, and polymeric material. According to the embodiments, the substrate comprises an integrated circuit, a MEMS device, a microarray, a macroarray, a multi-well plate, a micro fluidic device, or a combination thereof.

In on embodiment of the invention, the space for holding a sample comprises a reservoir, a microchannel, an opening, a surface, or a combination thereof. In another embodiment, the magnet comprises a permanent magnet or an electromagnet. The magnet may be placed near or adjacent to the space for holding a liquid sample. According to another embodiment, the microcoil comprises of copper, aluminum, gold, silver, or a mixture thereof. The microcoil is placed near or adjacent to the space for holding a liquid sample. Either Solenoid type or a planar spiral microcoil may be used.

In another embodiment of the invention, fabricating of the magnetic pattern on the disk comprises attaching one or more magnetic members on a surface of the disk. Further, the fabricating of the space may comprise fabricating an array of spaces for holding liquid samples on the substrate.

In a specific embodiment, fabricating of the magnetic pattern comprises attaching a plurality of magnetic members on a surface of the disk. According to the embodiment, the magnetic members are capable of generating an excitation magnetic field across each of at least two of the spaces. More specifically, fabricating of the microcoil comprises fabricating a microcoil associated with each of the at least two spaces such that the microcoil is capable of detecting the NMR or ESR signals from a liquid sample contained in the space.

As disclosed herein, silicon is a suitable material for attaching other materials, such as metal or magnetic materials and forming structures, such as openings and microchannels coupled with microelectronics or other microelectromechanical systems (MEMS). It also has good stiffness, allowing the formation of fairly rigid microstructures, which can be useful for dimensional stability. In a specific embodiment of the invention, the detection unit or substrate comprises an integrated circuit (IC), a packaged integrated circuit, and/or an integrated circuit die. For example, the substrate may be a packaged integrated circuit that comprises a microprocessor, a network processor, or other processing device.

In another embodiment, the method further comprises forming circuitry on or within the detection unit that is capable of amplifying or processing the NMR or ESR signals detected by the microcoil. The substrate for the detection unit may be constructed using, for example, a Controlled Collapse Chip Connection (or "C4") assembly technique, wherein a plurality of leads, or bond pads are internally electrically connected by an array of connection elements (e.g., solder bumps, columns).

In another embodiment of the invention, the fabricating of the microcoil comprises fabricating an array of microcoils capable of detecting NMR or ESR signals from at least a portion of the space. Further, each of at least a portion of an array of microcoils on the detection unit is capable of detecting NMR or ESR signals from a distinct portion of the space. In the embodiment, the substrate may comprise an array of spaces for holding liquid samples and each of at least a portion of the microcoils is capable of detecting NMR or ESR signals across one of the spaces. Thus, the embodiment encompasses fabricating an array of sample holding spaces each in association with a microcoil.

In the embodiments of the invention, the magnet may be attached either to or near the detection unit. The magnet, whether being a permanent magnet or an electromagnet, may be attached to a silicon substrate through an adhesive layer to form the detection unit. The adhesive layer can also be referred to and regarded as a seed layer used to join the magnet with the substrate. Any suitable adhesive materials may be used as the adhesive layer. In one embodiment of the invention, the adhesive layer comprises one or more of titanium, tantalum, platinum, and palladium.

According to the embodiments of the invention, microcoils can be fabricated on or within the substrate using a number of techniques, including etching, bonding, annealing, adhering/seeding, lithography, molding, and printing. Physical vapor deposition (PVD) and chemical vapor deposition (CVD) can also be used. In one embodiment, microcoils are fabricated on an oxidized silicon substrate by electroplating metals inside a deep photoresist mold and then passivated using an epoxy based resist.

The detection unit or substrate of the embodiments of the present invention is suitable for forming openings, voids, surfaces, or microchannels thereon for holding fluid and fluidic communications. The sample holding space may be open or closed along. Various methods may be used to form the sample holding space on the substrate. For example, a reservoir or an open microchannel can be fabricated on a silicon substrate by etching methods known to those skilled in the art. Closed microchannels can be formed by sealing the open channels at top using methods such as anodic bonding of glass plates onto the open microchannels on the silicon substrate.

According to one embodiment of the invention, to fabricate a microchannel on a silicon substrate, a photoresist (positive or negative) is spun onto the silicon substrate. The photoresist is exposed to UV light through a high-resolution mask with the desired device patterns. After washing off the excessive unpolymerized photoresist, the silicon substrate is placed in a wet chemical etching bath that anisotropically etches the silicon in locations not protected by the photoresist. The result is a silicon substrate in which microchannels are etched. If desired, a glass cover slip is used to fully enclose the channels. Also, holes are drilled in the glass to allow fluidic access. For straighter edges and a deeper etch depth, deep reactive ion etching (DRIE) can be used as an alternative to wet chemical etching.

In another embodiment of the invention, microchannels may be formed on a silicon substrate using the following method. A seed layer of a metal, such as copper, is deposited over a surface of the substrate. Any suitable blanket deposition process may be used to deposit the seed layer of metal, such as physical vapor deposition (PVD), chemical vapor deposition (CVD), or other methods known to those skilled in the art. A layer of a sacrificial material, such as a dielectric material or a photoresist material, is then deposited over the seed layer. By removing the sacrificial material, for example using chemical etch process or thermal decomposition process, a number of trenches in the sacrificial layer is formed, and the seed layer is exposed in each of the trenches. Another layer of the metal, such as copper, is deposited over the exposed seed layer in the trenches. The metal layer extends over portions of the upper surface of the sacrificial layer; but gaps remain between the metal material layers extending from adjacent trenches and over the upper surface of the sacrificial layer. The sacrificial layer is removed, for example using chemical etching process or thermal decomposition process, and regions from which the sacrificial layer has been removed form channels in the metal layer. An additional layer of the metal is deposited over the upper surfaces of the metal layer to close the gaps over the channels.

In the embodiments of the invention, reservoirs, openings and microchannels can be made by using soft lithography method with suitable materials, such as silicon and polydimethylsiloxane (PDMS). With these techniques it is possible to generate patterns with critical dimensions as small as 30 nm. These techniques use transparent, elastomeric PDMS "stamps" with patterned relief on the surface to generate features. The stamps can be prepared by casting prepolymers against masters patterned by conventional lithographic techniques, as well as against other masters of interest. Several different techniques are known collectively as soft lithography. They are as described below:

Near-Field Phase Shift Lithography. A transparent PDMS phase mask with relief on its surface is placed in conformal contact with a layer of photoresist. Light passing through the stamp is modulated in the near-field. Features with dimensions between 40 and 100 nm are produced in photoresist at each phase edge.

Replica Molding. A PDMS stamp is cast against a conventionally patterned master. Polyurethane is then molded against the secondary PDMS master. In this way, multiple copies can be made without damaging the original master. The technique can replicate features as small as 30 nm.

Micromolding in Capillaries (MIMIC). Continuous channels are formed when a PDMS stamp is brought into conformal contact with a solid substrate. Capillary action fills the channels with a polymer precursor. The polymer is cured and the stamp is removed. MIMIC is able to generate features down to 1 µm in size.

Microtransfer Molding ((TM). A PDMS stamp is filled with a prepolymer or ceramic precursor and placed on a substrate. The material is cured and the stamp is removed. The technique generates features as small as 250 nm and is able to generate multilayer systems.

Solvent-assisted Microcontact Molding (SAMIM). A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontact Printing ((CP). An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used in other groups include micromachining of silicon for microelectromechanical systems, and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm.

Standard lithography on silicone wafer or silica glass could also be used to fabricate the devices of the embodiments of this invention. Reservoirs, openings and channels in the micrometer or nanometer scale can be fabricated from the devices, and fluidic flow can be controlled by pressure gradient, electrical field gradient, gravity, and heat gradient. The binding complexes or sensors can also be separated by planar device with a single a plurality of chambers, where the surfaces are modified with polymers (polyethylene glycol (PEG)-dramatized compounds) that can minimize nonspecific binding. The solid support can be inorganic material (e.g., glass, ceramic) or metal (e.g., aluminum). Biomolecules, proteins, antibodies, and/or nucleic acids can be coated on the surface of the substrate for specific analyte binding.

In the embodiments of the invention, the microchannels formed on the substrate may be straight or have angles or curves along their lengths. The characteristics and layout of the microchannels are determined by the specific applications the device is designed for. Although straight microchannels lining next to one another are a typical design for microfluidic devices, the microchannels in the embodiments of the invention may be designed in many different patterns to serve specific separation and detection requirements. Specifically, the design of the microchannels takes into consideration of the microcoils associated with the microchannels such that the microcoils are capable of generating excitation magnetic fields across relevant portions of the microchannels. Further, in the embodiments of the invention, the cross-section of the micro-channel so formed may be uniform or vary along the channel's length, and may have various shapes, such as rectangle, circle, or polygon.

EXAMPLES

The rotation speed and dimension of the disk and magnetic patterns on disk (MPoD) were obtained using model calculations. The calculations are based upon the assumption that the duration of magnetic pulse is 10 microsecond ($\mu$sec) and acquisition time is 160 millisecond (msec), similar as described in C. Massin et al., "*High-Q Factor RF Planar Microcoilsfor Micro-Scale NMR Spectroscopy,*" *Sensors and Actuators* A 97-98, 280-283 (2002) work by C. Massin et al. The purpose of the calculations is to determine the rotation speed and the length of the MPoD in the direction along the tracks.

Rotation Speed:

The rotation speed to allow for acquisition time long enough to capture the decay process induced by magnetic resonance was determined. Assuming there was only one sample holding space on the detection unit or RDU, one revolution of disk should take at least 160 msec. This relationship translates into 375 rotations per minute (rpm):

1 rotation per 160 msec=375 rpm

The disk should operate slower than 375 rpm. For comparison, typical floppy disk drive systems run at 300-360 rpm.

Magnetic Pattern Size:

The size of a magnetic member in the MPoD required to generate a 10 $\mu$sec-long pulse was calculated. For simplicity of calculation, the track at a distance of 3 cm from center of the disk was considered. Using the rotation speed of 375 rpm at a track at 3 cm from center of disk center, a single rotation corresponds to 160 msec and 18.85 cm in linear travel distance. During 10 $\mu$sec, a point on the track travels 11.78 $\mu$m. Thus, in order to obtain pulse with duration of 10 $\mu$sec, the magnetic member should be about 11.78 $\mu$m in length (along the track).

Material Choice for MPoD:

Co alloy can be used to fabricate MPoD. Perpendicularly oriented Co-alloy film will provide excitation by generating magnetic pulse to the sample of interest as disk rotates. Other magnetic films with perpendicular anisotropy can be also used. Such films include but are not limited to Co/Pt and Co/Pd multi-layers.

The characteristics of some of the embodiments of the invention are illustrated in the Figures and examples, which are intended to be merely exemplary of the invention. This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising:
   a detection unit comprising a space for holding a sample and a microcoil;
   a magnet to generate a static magnetic field across at least a portion of the space; and
   a disk comprising a magnetic pattern to generate an excitation magnetic field across at least a portion of the space;
   wherein the static magnetic field and the excitation magnetic field are capable of creating Nuclear Magnetic Resonance (NMR) or Electron Spin Resonance (ESR) within a liquid sample contained in the space; and
   wherein the microcoil is capable of detecting signals from the NMR or ESR.

2. The device of claim 1, wherein the detection unit comprises silicon, glass, a polymeric material, metal, or a combination thereof.

3. The device of claim 1, wherein the detection unit comprises an integrated circuit, a MEMS device, a microarray, a macroarray, a multi-well plate, a microfluidic device, or a combination thereof.

4. The device of claim 1, wherein the detection unit comprises circuitry capable of amplifying or processing the NMR and ESR signals detected by the microcoil.

5. The device of claim 1, wherein the detection unit is connected to a circuitry capable of amplifying or processing the NMR and ESR signals detected by the microcoil.

6. The device of claim 1, wherein the sample is a liquid, a gel, a solid, a gas, or a mixture thereof.

7. The device of claim 1, wherein the space for holding a sample comprises a reservoir, a microchannel, an opening, a surface, or a combination thereof.

8. The device of claim 7, wherein the space for holding a sample is a microchannel, the microchannel having two or more inlets, at least one outlet, and at least one mixing section where liquid samples introduced from the two or more inlets can be mixed.

9. The device of claim 1, wherein the space for holding a sample has a volume of from about 1.0 nL to about 1.0 mL.

10. The device of claim 9, wherein the space for holding a sample has a volume of from about 10 nL to about 10 $\mu$L.

11. The device of claim 1, wherein the microcoil comprises copper, aluminum, gold, silver, or a mixture thereof.

12. The device of claim 1, wherein the microcoil is placed near or adjacent to the space for holding a liquid sample.

13. The device of claim 1, wherein the microcoil is a Solenoid type coil.

14. The device of claim 1, wherein the microcoil is a planar spiral coil.

15. The device of claim 1, wherein the magnet is located on the detection unit.

16. The device of claim 1, wherein the magnet comprises a permanent magnet or an electromagnet.

17. The device of claim 1, wherein the magnet is capable of generating a uniform static magnetic field across a substantial portion of the space.

18. The device of claim 1, wherein the magnet is capable of generating a static magnetic field strength of from about 0.01 Tesla (T) to about 30 T.

19. The device of claim 1, wherein the magnet is capable of generating a static magnetic field strength of from about 0.5 T to about 5.0 T.

20. The device of claim 1, wherein the magnet is capable of generating a static magnetic field strength of from about 0.01 T to about 0.5 T.

21. The device claim 1, wherein the disk comprises metal, polymer, silicon, glass, or a combination thereof.

22. The device of claim 21, wherein the disk comprises aluminum, gold, copper, silver, cobalt, platinum, chromium, iron, a metal oxide, a polycarbonate, or a combination thereof.

23. The device of claim 1, wherein the disk has a diameter ranging from about 1.0 cm to about 20 cm.

24. The device of claim 1, wherein the disk has a diameter ranging from about 2.0 cm to about 10 cm.

25. The device of claim 1, wherein the disk is capable of storing data related to the NMR or ESR signal.

26. The device of claim 1, wherein the magnetic pattern comprises one or more magnetic members attached to a surface of the disk, each of the magnetic members occupying an area on the surface of the disk and having a thickness measured by the biggest perpendicular distance from a point on the magnetic member to the surface of the disk.

27. The device of claim 26, wherein the magnetic members comprise iron, nickel, cobalt, copper, aluminum, platinum, palladium, or a combination thereof.

28. The device of claim 26, wherein the area has a circular, rectangular, or cubical shape.

29. The device of claim 26, wherein the area has a dimension ranging from about 1.0 nm to about 1000 mm.

30. The device of claim 29, wherein the area has a dimension ranging from about 0.1 µm to about 1000 µm.

31. The device of claim 26, wherein the thickness ranges from 1.0 nm to about 500 mm.

32. The device of claim 26, wherein the thickness ranges from 10 nm to about 1000 µm.

33. The device of claim 26, wherein there is only one magnetic member located at a given distance from the center of the disk.

34. The device of claim 26, wherein there are two or more magnetic members located at a given distance from the center of the disk.

35. The device of claim 26, wherein the distances from the magnetic members to the center of the disk range from about 1.0 cm to about 20 cm.

36. The device of claim 26, wherein the distances from the magnetic members to the center of the disk range from about 2.0 cm to about 10 cm.

37. The device of claim 1, further comprising a servomechanical component capable of controlling the location and movement of the detection unit, the magnet, or the disk.

38. The device of claim 1, wherein the detection unit comprises an array of spaces for holding liquid samples.

39. The device of claim 37, wherein the magnetic pattern on the disk is capable of generating an excitation magnetic field across at least two of the spaces.

40. The device of claim 39, wherein the magnet is capable of generating a static magnetic field across the at least two spaces.

41. The device of claim 40, wherein the static magnetic field and the excitation magnetic field are capable of creating NMR or ESR within a liquid sample contained in each of the at least two spaces.

42. The device of claim 41, wherein each of at least two of the spaces is associated with a microcoil capable of detecting the NMR or ESR signals.

43. The device of claim 38, wherein each of the spaces has a volume of from about 10 nL to about 100 µL.

44. A method comprising:
providing a device, the device comprising a detection unit, a magnet, and a disk, wherein the detection unit comprises a space for holding a sample and a microcoil, and the disk comprises a magnetic pattern;
providing a sample within the space;
using the magnet to generate a static magnetic field across at least a portion of the sample;
rotating the disk to generate an excitation magnetic field across at least a portion of the sample; and
detecting signals from the sample by using the microcoil.

45. The method of claim 44, wherein the static magnetic field and the excitation magnetic field create Nuclear Magnetic Resonance (NMR) or Electron Spin Resonance (ESR) within the liquid sample.

46. The method of claim 44, further comprising amplifying, processing, or analyzing the signals detected by the microcoil.

47. The method of claim 44, wherein the sample is a liquid, a gel, a solid, a gas, or a mixture thereof.

48. The method of claim 44, further comprising generating an NMR or ESR spectroscopy of the sample.

49. The method of claim 44, further comprising storing data related to the NMR or ESR signals in the disk.

50. The method of claim 44, the providing of the device comprises using a servomechanism to control the location and movement of the detection unit, the magnet, or the disk.

51. The method of claim 44, wherein the rotating of the disk is at a speed of from about 10 rpm to about 2000 rpm.

52. The method of claim 44, wherein the rotating of the disk is at a speed of from about 100 rpm to about 1000 rpm.

53. The method of claim 44, wherein the providing the sample within the space comprises introducing two or more different samples into the space.

54. A method comprising:
fabricating a space for holding a sample on a substrate;
fabricating a microcoil on the substrate, the microcoil being associated with the space;
attaching a magnet to the substrate, the magnet being capable of generating a static magnetic field across at least a portion of the space; and
fabricating a magnetic pattern on a disk, the magnetic pattern being capable of generating an excitation magnetic field across at least a portion of the space;
wherein the static magnetic field and the excitation magnetic field are capable of creating Nuclear Magnetic Resonance (NMR) or Electron Spin Resonance (ESR) within a sample contained in the space; and wherein the microcoil is capable of detecting signals from the NMR or ESR.

55. The method of claim 54, wherein fabricating of the space or the fabricating of the microcoil comprises combining two or more solid support to form the substrate.

56. The method of claim 54, wherein the sample is a liquid, a gel, a solid, a gas, or a mixture thereof.

57. The method of claim 54, further comprising forming circuitry on the substrate, the circuitry being capable of amplifying or processing the NMR or ESR signals detected by the microcoil.

58. The method of claim 54, wherein fabricating the magnetic pattern on the disk comprises attaching one or more magnetic members on a surface of the disk.

59. The method of claim 54, wherein fabricating of the space comprises fabricating an array of spaces for holding samples on the substrate.

60. The method of claim 59, wherein fabricating of the magnetic pattern comprises attaching a plurality of magnetic members on a surface of the disk, the magnetic members being capable of generating an excitation magnetic field across each of at least two of the spaces.

61. The method of claim 60, wherein fabricating of the microcoil comprises fabricating a microcoil associated with each of the at least two spaces, the microcoil being capable of detecting the NMR or ESR signals from a liquid sample contained in the space.

62. The method of claim 54, further comprising providing servo-mechanical components to control the locations and movements of the substrate, the magnet, and the disk.

* * * * *

UNITED STATES PATENT AND TRADEMARK OFFICE
CERTIFICATE OF CORRECTION

PATENT NO. : 7,319,323 B2 Page 1 of 1
APPLICATION NO. : 11/394160
DATED : January 15, 2008
INVENTOR(S) : Park et al.

It is certified that error appears in the above-identified patent and that said Letters Patent is hereby corrected as shown below:

In column 29, line 10, in Claim 21, delete "device" and insert -- device of --, therefor.

In column 30, line 31, in Claim 50, delete "the" and insert -- wherein the --, therefor.

In column 30, line 38, in Claim 53, delete "providing" and insert -- providing of --, therefor.

Signed and Sealed this

Second Day of September, 2008

JON W. DUDAS
*Director of the United States Patent and Trademark Office*